(12) United States Patent
Barberousse et al.

(10) Patent No.: US 6,602,899 B1
(45) Date of Patent: Aug. 5, 2003

(54) β-D-5 THIOXYLOSE DERIVATIVES, PREPARATION METHOD AND THERAPEUTIC USE

(75) Inventors: Véronique Barberousse, Hauteville les Dijon (FR); Benaïssa Boubia, Saint Apollinaire (FR); Soth Samreth, Daix (FR)

(73) Assignee: Fournier Industrie & Sante, Chenove (FR)

( * ) Notice: Subject to any disclaimer, the term of this patent is extended or adjusted under 35 U.S.C. 154(b) by 0 days.

(21) Appl. No.: 10/129,899

(22) PCT Filed: Nov. 15, 2000

(86) PCT No.: PCT/FR00/03174

§ 371 (c)(1),
(2), (4) Date: May 9, 2002

(87) PCT Pub. No.: WO01/36437

PCT Pub. Date: May 25, 2001

(30) Foreign Application Priority Data

Nov. 17, 1999 (FR) .............................. 99 14445

(51) Int. Cl.$^7$ ........................ A61K 31/38; A61K 31/70; C07D 335/02; C07H 15/24
(52) U.S. Cl. ........................ 514/432; 514/27; 514/25; 549/28; 536/18.1; 536/14.1
(58) Field of Search ............................ 514/25, 27, 432; 536/4.1, 18.1; 549/28

(56) References Cited

U.S. PATENT DOCUMENTS 5,169,838 A * 12/1992 Samreth et al. ............... 514/27

FOREIGN PATENT DOCUMENTS

EP 0 421 829 4/1991

* cited by examiner

*Primary Examiner*—Deborah C. Lambkin
(74) *Attorney, Agent, or Firm*—Merchant & Gould P.C.

(57) ABSTRACT

The invention concerns a 4-methyl-2-oxo-2H-1-benzopyran-7-yl 5-thio-β-D-xylopyranoside compound of formula (I):

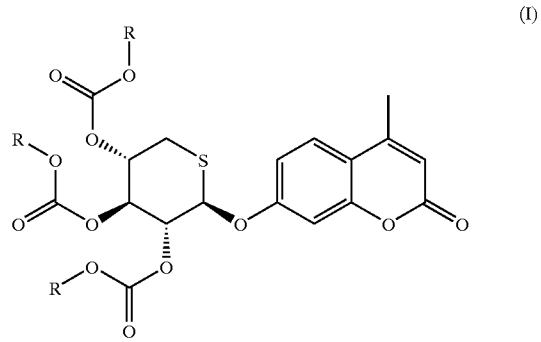

wherein:

R represents a $C_1$–$C_5$-alkyl group, which is liner, branched or cyclized, a mono-unsaturated $C_2$–$C_3$-alkene group, a $C_2$–$C_3$-hydroxyalkyl group or a $C_3$–$C_6$-alkoxyalkyl group. The invention also concerns the method for preparing said compound and the therapeutic use thereof as antithrombic substance.

10 Claims, No Drawings

β-D-5 THIOXYLOSE DERIVATIVES, PREPARATION METHOD AND THERAPEUTIC USE

This application is a 371 of PCT/FR00/03174 filed Nov. 15, 2000.

The present invention relates, by way of novel industrial products, to β-D-5-thioxylose derivatives, more particularly to the 4-methyl-2-oxo-2H-1-benzopyran-7-yl 5-thio-β-D-xylopyranoside derivatives of formula I below. It further relates to the method for the preparation of these novel products and to their use in therapeutics.

Prior Art

EP-A-0421829, especially Table I of said document, discloses benzopyranone β-D-thioxyloside compounds of formula Io:

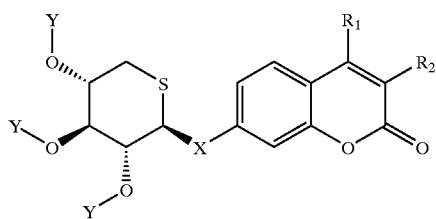

in which:
 X is O or S,
 Y is especially H or $COCH_3$,
 $R_1$ is especially $C_1$–$C_4$-alkyl and
 $R_2$ is particularly H, $C_1$–$C_4$-alkyl or halogen, which are presented as being useful in therapeutics in view of their effects in the prevention or treatment of disorders of the venous circulation, especially venous thrombosis.

In particular, the compound 4-methyl-2-oxo-2H-1-benzopyran-7-yl 5-thio-β-D-xylopyranoside (formula Io in which X=O, Y=H, $R_1$=$CH_3$ and $R_2$=H), administered orally, exhibits a remarkable activity at doses of 6 mg/kg and above in the sense that it reduces the formation of a venous thrombus by more than 80%. This activity, which is obtained after oral administration, is extremely valuable in the case of the most common use of such products, which generally corresponds to a preventive treatment.

In fact, the products commonly used at the present time in this field of therapeutics, for example anticoagulants, namely normal heparins and low molecular heparins, are not active by oral administration and have to be administered by intravenous or subcutaneous injection. Such a mode of administration, especially in a chronic treatment, is not generally liked by the patient, who prefers to take a tablet or a gelatin capsule orally. From this point of view, the compounds according to EP-A-0421829 represent a certain advance in terms of the patient's comfort, the risk and the costs associated with the mode of administration. It should also be pointed out that, in contrast to the products already in use, these compounds do not increase the risk of a hemorrhage.

However, the compounds described in EP-A-0421829 are not sufficiently soluble to allow them to be administered by injection. Thus they cannot be used in cases where injection is the only possible route of administration or if it seems preferable for the sake of convenience to administer one of these compounds in association with other drugs by perfusion.

Object of the Invention

According to the invention, a novel technical solution is proposed for solving the above-mentioned solubility problem. This novel solution involves novel 4-methyl-2-oxo-2H-1-benzopyran-7-yl 5-thio-β-D-xylopyranoside derivatives which have a better solubility in the customary solvents, especially injectable solutions, while at the same time retaining an oral activity.

Subject of the Invention

The invention provides, by way of a novel industrial product, a compound which is characterized in that it has formula I:

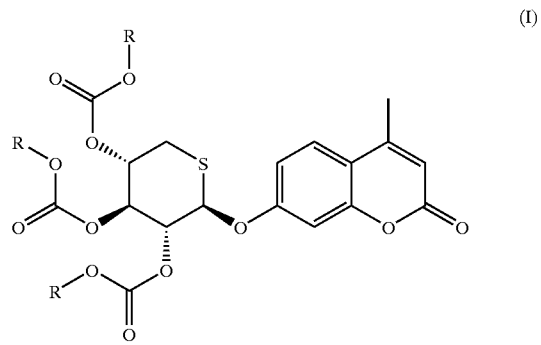

in which R is a linear, branched or cyclic $C_1$–$C_5$-alkyl group, a monounsaturated $C_2$–$C_3$-alkene group, a $C_2$–$C_3$-hydroxyalkyl group or a $C_3$–$C_6$-alkoxyalkyl group.

According to another feature of the invention, the method for the preparation of a compound of formula I is provided, said method being characterized in that it comprises the carbonation reaction of 4-methyl-2-oxo-2H-1-benzopyran-7-yl 5-thio-β-D-xylopyranoside of formula II:

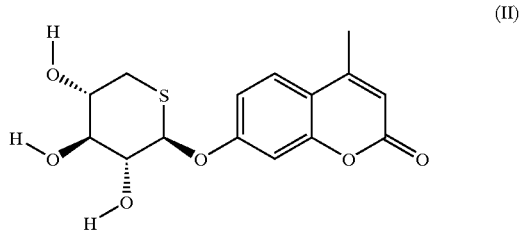

with a reagent selected from the group consisting of a halogenoformate of formula III:

and a pyrocarbonate of formula IV:

in which R is a $C_1$–$C_5$-alkyl group, a $C_2$–$C_3$-alkene group, a $C_3$–$C_6$-alkoxyalkyl group or a $C_2$–$C_3$-hydroxyalkyl group in which the alcohol function is protected by a protecting group, such as a trialkylsilyl group for example, and Hal is a halogen atom (especially F, Cl or Br, the preferred halogen here being chlorine).

This method involves protecting the OH function of the group R=C$_2$–C$_3$-hydroxyalkyl before carbonation and then deprotecting it after said carbonation.

The procedure is as follows, depending on the nature of the group R. When R=R'=a linear, branched or cyclic C$_1$–C$_5$-alkyl group, a monounsaturated C$_2$–C$_3$-alkene group or a C$_3$–C$_6$-alkoxyalkyl group, the reaction II+III or II+IV is carried out.

When R=R"=a C$_2$–C$_3$-hydroxyalkyl group, the carbonation reaction of 4-methyl-2-oxo-2H-1-benzopyran-7-yl 5-thio-β-D-xylopyranoside of formula II is carried out with a halogenoformate of formula IIIbis:

(IIIbis)

in which R" is a C$_2$–C$_3$-hydroxyalkyl group with its OH function protected and Hal is a halogen atom as defined above, and the resulting compound is then subjected to a deprotection reaction of the hydroxyl group, for example by reaction with hydrofluoric acid solution if the protecting group is a trialkylsilyl group, to give the compound of formula I in which R is a C$_2$–C$_3$-hydroxyalkyl group.

According to yet another feature of the invention, on the one hand a pharmaceutical composition is provided which is characterized in that it comprises a therapeutically effective amount of at least one compound of formula I in association with a physiologically acceptable excipient, and on the other hand the use of a compound of formula I is provided which is characterized in that said compound of formula I is used for obtaining an antithrombotic drug intended for therapeutic use to combat disorders of the venous circulation.

Detailed Description of the Invention

Methyl, ethyl, propyl, 1-methylethyl, cyclopropyl, butyl, 1-methylpropyl, 2-methylpropyl, 1,1-dimethylethyl and pentyl groups may be mentioned among the C$_1$–C$_5$-alkyl groups which are suitable according to the invention.

Vinyl and allyl groups may be mentioned among the C$_2$–C$_4$-alkene groups which are suitable according to the invention. In this case a monounsaturated alkene group denotes an aliphatic group containing only one C=C double bond.

Methoxyethyl, ethoxyethyl, methoxyethoxyethyl and ethoxyethoxyethyl groups may be mentioned among the C$_3$–C$_6$-alkoxyalkyl groups which are suitable according to the invention.

2-Hydroxyethyl, 2-hydroxypropyl or 3-hydroxypropyl groups may be mentioned among the C$_2$–C$_3$-hydroxyalkyl groups which are suitable according to the invention.

Among the compounds of formula I, which are 4-methyl-2-oxo-2H-1-benzopyran-7-yl 5-thio-β-D-xylopyranoside tricarbonates, those in which R is an ethyl group or a methyl group are preferred.

The compounds of formula I can advantageously be prepared by means of a) a carbonation reaction in which 4-methyl-2-oxo-2H-1-benzopyran-7-yl 5-thio-β-D-xylopyranoside of formula II:

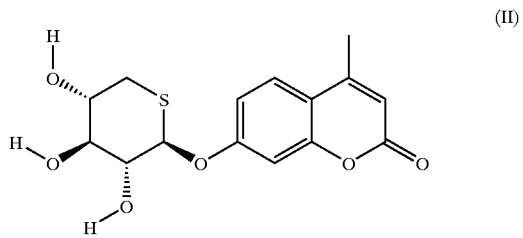

(II)

is reacted with a chloroformate of formula IIIa:

(IIIa)

or a pyrocarbonate of formula IV:

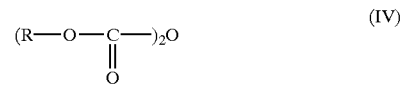

(IV)

in which R is a linear, branched or cyclic C$_1$–C$_5$-alkyl group, a monounsaturated C$_2$–C$_3$-alkene group, a C$_3$–C$_6$-alkoxyalkyl group or a C$_2$–C$_3$-hydroxyalkyl group in which the hydroxyl group is protected by a protecting group, especially the t-butyldimethylsilyl group, the reaction being carried out in an anhydrous solvent, such as dimethylformamide for example, in the presence of an aprotic base, such as 4-(dimethylamino)pyridine for example, at a temperature of between 10° C. and 80° C. for 1 to 10 hours to give the compound of formula I in which R retains the same meaning as in the reagent IIIa or IV; and b) if necessary, in the case of the preparation of a compound of formula I in which R is a hydroxyalkyl group, a deprotection reaction of the hydroxyl group, especially by reaction with hydrofluoric acid if the protecting group is a t-butyldimethylsilyl group, at room temperature, in a solvent such as acetonitrile for example.

When R is a C$_2$–C$_3$-hydroxyalkyl group, the carbonation reaction is preferably effected by means of a chloroformate. The protecting group of the OH function must be more readily cleavable than the O—CO—O function so that it can be removed during deprotection without affecting said O—CO—O function, the preferred protecting group being a trialkylsilyl group.

The therapeutic composition can be in the form of a solution, or a preparation convertible to a solution, which can be administered by injection, either subcutaneously, or intravenously, or in the form of a perfusion. The therapeutic composition can also be presented in a form which can be administered orally, for example gelatin capsules, tablets or a solution to be taken orally.

The compounds of formula I are useful in therapeutics on account of their antithrombotic activity and are of particular value for the treatment or prevention of disorders of the venous circulation, especially for correcting certain hematological parameters perceptible in the venous system.

The Examples which follow, together with the results of pharmacological tests, which in no way imply a limitation, will afford a better understanding of the value of the invention.

EXAMPLE 1

4-Methyl-2-oxo-2H-1-benzopyran-7-yl 2,3,4-tri-O-methoxycarbonyl-5-thio-β-D-xylopyranoside A solution of 2 g (6.17.10$^{-3}$ mol) of 4-methyl-2-oxo-2H-1-benzopyran-7-yl 5-thio-β-D-xylopyranoside in 20 ml of dimethylformamide is prepared at 70° C. and then cooled to about 25° C. 10 mg ($0.8.10^{-3}$ mol) of 4-dimethylaminopyridine are added, followed by 3.85 ml ($36.10^{-3}$ mol) of dimethyl pyrocarbonate. After stirring for 4 hours at room temperature (15–25° C.), a further 3.85 ml of dimethyl pyrocarbonate are added and the reaction medium is stirred at room temperature for 6 hours. The mixture is then filtered and concentrated under reduced pressure and the residue is purified by chromatography on silica gel using a toluene/acetone mixture (6/1; v/v) as the eluent. The pure fraction is crystallized from an acetone/ether mixture, filtered off and dried to give 1.92 g of the expected product in the form of a white powder (yield=63%).

M.p.=168° C.; $[\alpha]_D^{21}$=−77° (c=0.37; CHCl$_3$).

EXAMPLE 2

4-Methyl-2-oxo-2H-1-benzopyran-7-yl 2,3,4-tri-O-ethoxycarbonyl-5-thio-β-D-xylopyranoside The expected product is obtained in the form of a white powder (yield=78%) by following a procedure analogous to Example 1 except that the dimethyl pyrocarbonate is replaced with diethyl pyrocarbonate.

M.p.=176° C.; $[\alpha]_D^{22}$=−72° (c=0.465; CHCl$_3$).

EXAMPLE 3

4-Methyl-2-oxo-2H-1-benzopyran-7-yl 2,3,4-tri-O-propoxycarbonyl-5-thio-β-D-xylopyranoside A solution of 100 mg ($0.8.10^{-3}$ mol) of 4-dimethylaminopyridine in 12 ml of pyridine is prepared and 2.1 ml ($18.7.10^{-3}$ mol) of propyl chloroformate are added at 0° C., followed by 1 g ($3.1.10^{-3}$ mol) of 4-methyl-2-oxo-2H-1-benzopyran-7-yl 5-thio-β-D-xylopyranoside. The reaction mixture is stirred for 1 hour, a further 1 ml ($8.9.10^{-3}$ mol) of propyl chloroformate is then added and stirring is continued for 1 hour. The mixture is then hydrolyzed in ice water and extracted with ethyl acetate. The organic phase is washed with dilute hydrochloric acid solution and then with water, dried and finally concentrated under reduced pressure. The residue is purified by chromatography on silica gel using a toluene/ethyl acetate mixture (4/1; v/v) as the eluent. The pure product fraction is crystallized from an ethyl acetate/ diethyl ether mixture to give 1.13 g of the expected product in the form of a fine and light white solid (yield=63%).

M.p.=134° C.; $[\alpha]_D^{23}$=−57° (c=0.37; CHCl$_3$).

EXAMPLE 4

4-Methyl-2-oxo-2H-1-benzopyran-7-yl 2,3,4-tri-O-butoxycarbonyl-5-thio-β-D-xylopyranoside The expected product is obtained in the form of a white cottony solid (yield=85%), after crystallization from diethyl ether, by following a procedure analogous to Example 3 except that the propyl chloroformate is replaced with butyl chloroformate.

M.p.=120° C.; $[\alpha]_D^{23}$=−51° (c=0.45; CHCl$_3$).

EXAMPLE 5

4-Methyl-2-oxo-2H-1-benzopyran-7-yl 2,3,4-tri-O-(2-methylpropoxycarbonyl)-5-thio-β-D-xylopyranoside The expected product is obtained in the form of a fine white solid (yield=89%) by following a procedure analogous to Example 3 except that the propyl chloroformate is replaced with 2-methylpropyl chloroformate.

M.p.=114° C.; $[\alpha]_D^{23}$=−43° (c=0.415; CHCl$_3$).

EXAMPLE 6

4-Methyl-2-oxo-2H-1-benzopyran-7-yl 2,3,4-tri-O-(2-methoxyethoxycarbonyl)-5-thio-β-D-xylopyranoside The expected product is obtained in the form of a light white powder (yield=80%) by following a procedure analogous to Example 3 except that the propyl chloroformate is replaced with 2-methoxyethyl chloroformate.

M.p.=118° C.; $[\alpha]_D^{23}$=−69° (c=0.65; CHCl$_3$).

EXAMPLE 7

4-Methyl-2-oxo-2H-1-benzopyran-7-yl 2,3,4-tri-O-(2-propenylcarbonyl)-5-thio-β-D-xylopyranoside The expected product is obtained in the form of a pulverulent white solid (yield =8%) by following a procedure analogous to Example 3 except that the propyl chloroformate is replaced with allyl chloroformate.

M.p.=120° C.; $[\alpha]_D^{22}$=−57° (c=0.46; CHCl$_3$).

EXAMPLE 8

4-Methyl-2-oxo-2H-1-benzopyran-7-yl 2,3,4-tri-O-(ethenyloxycarbonyl)-5-thio-β-D-xylopyranoside The expected product is obtained in the form of a white powder (yield=57%) by following a procedure analogous to Example 3 except that the propyl chloroformate is replaced with vinyl chloroformate.

M.p.=120° C.; $[\alpha]_D^{23}$=−45° (c=0.47; CHCl$_3$).

PREPARATION I

2[[(1,1-Dimethylethyl)dimethylsilyl]oxy]ethyl Chloroformate

A solution of 3.1 g (17.6 $10^{-3}$ mol) of 2-[[(1,1-dimethylethyl)dimethylsilyl]oxy]ethanol and 1.3 ml ($19.3.10^{-3}$ mol) of pyridine in 15 ml of dichloromethane is prepared and this solution is added dropwise to a mixture of 10 ml of a 20% solution of phosgene in toluene (i.e. $19.3.10^{-3}$ mol of phosgene) and 10 ml of dichloromethane, cooled to 0° C. When the addition has ended, the reaction medium is stirred for 2 hours and then brought back to room temperature. A stream of argon is then bubbled into the mixture for 30 min to drive off the residual phosgene. The residual solution is used directly for the next synthesis step.

PREPARATION II

4-Methyl-2-oxo-2H -1-benzopyran-7-yl 2,3,4-tri-O-[[2-[[(1,1-dimethylethyl)-dimethylsilyi]oxy]ethoxy]carbonyl]-5-thio-β-D-xylopyranoside A solution of 500 mg ($1.5.10^{-3}$ mol) of 4-methyl-2-oxo-2H-1-benzopyran-7-yl 5-thio-β-D-xylopyranoside and 50 mg ($0.41.10^{-3}$ mol) of 4dimethylamino)pyridine in 25 ml of pyridine is prepared. This solution is added dropwise to the chloroformate solution obtained in Preparation I, with stirring. The reaction mixture is then stirred for 18 hours at room temperature. 50 ml of dichloromethane and 100 ml of water are then added. The phases are separated and the aqueous phase is extracted with 50 ml of dichloromethane The combined organic phases are washed with water and then dried over magnesium sulfate and concentrated under reduced pressure. The residue is purified by chromatography on silica gel using an ethyl acetate/hexane mixture (3/7; v/v) as the eluent to give 1.13 g of the expected product in the form of a light yellow pasty solid (yield 79%).

EXAMPLE 9

4-Methyl-2-oxo-2H-1-benzopyran-7-yl 2,3,4-tri-O-(2-hydroxyethoxycarbonyl)-5-thio-β-D-xylopyranoside 880 mg ($0.95.10^{-3}$ mol) of the compound obtained according to Preparation II are dissolved in 40 ml of acetonitrile, and 0.25 ml of 40% hydrofluoric acid is added. The reaction mixture is stirred for 5 minutes at room temperature and then concentrated under reduced pressure. The residue is chromatographed on silica gel using a dichloromethane/methanol mixture (9/1; v/v) as the eluent to give 486 mg of the expected product in the form of a white powder (yield=87%).

M.p.=97–98° C.; $[\alpha]_D^{25}=-76°$ (c=0.35; CHCl$_3$).

The pharmacological activity of some of the compounds according to the invention was demonstrated by means of a test which reproduces venous thrombosis and whose operating protocol is as follows:

The experiments are performed on non-fasted Wistar male rats weighing 250 to 280 g, divided into groups of 10 animals each. The test products are administered either orally (tubage) dissolved or suspended in PEG 400, or by intravenous injection dissolved in PEG 400. The concentration of the compounds is calculated so that the amount of solution absorbed is 2 ml/kg by oral administration and 1 ml/kg by intravenous injection. The compounds are generally administered intravenously at a dose of 5 mg/kg. If the test is performed after oral administration, the amount administered is calculated so as to correspond to about $2.10^{-5}$ mol/kg. Thrombosis is induced at a time T (2 h, 4 h or 8 hours) after the administration of the product, and the thrombus formed is removed and weighed. To induce this thrombosis, a venous stasis is created under hypercoagulation according to the technique described by WESSLER (J. Applied Physiol. 1959, pp. 943–946), the hypercoagulating agent used being a solution of activated factor X (Xa) having a concentration of 7.5 nKat/kg, supplied by Biogenic. The results obtained, expressed as the percentage inhibition calculated relative to the weight of a thrombus obtained in the absence of active principle in the vehicle, are collated in Table I below. The activity of the test compounds was checked at different doses after they had been administered either orally (p.o.) or intravenously (i.v.). The thrombosis was induced 4 hours or 8 hours after oral administration of the compound and 2 hours after intravenous administration. By way of comparison, Table I also shows the results obtained with 4-methyl-2-oxo-2H-benzopyran-7-yl 5-thio-β-D-xylopyranoside, which is described in EP-A-0421829 cited above and is referred to as D in said Table I (this compound is insoluble in injectable solvents, especially water and PEG 400, and cannot be administered intravenously).

After intravenous administration, the compounds according to the invention exhibit an antithrombotic activity which is substantially equivalent to that obtained by oral administration of the comparison product D, although the onset of action is more rapid. These compounds, which retain a good activity by oral administration, can be presented either in injectable form in order to obtain a rapid effect, or in an orally absorbable form in order to avoid the trouble or risks associated with repeat injections.

They can be formulated with physiologically acceptable excipients to give a directly injectable form, an injectable form to be prepared immediately before use, or a solid form for oral administration, for example a gelatin capsule or a tablet, each unit containing about 25 to 500 mg of at least one of the compounds of formula I.

TABLE I (I)

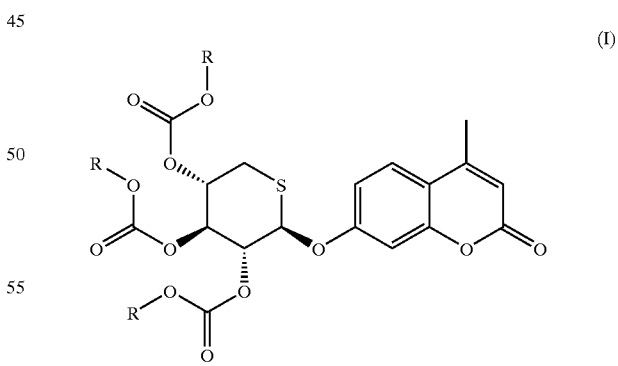

| Product | R | Activity i.v. (mg/kg) T = 2 h | Activity p.o. (mg/kg) T = 4 h | Activity p.o. (mg/kg) T = 8 h |
|---|---|---|---|---|
| Ex. 1 | —CH$_3$ | 84% (5) | 87% (9) | 66% (9) |
| Ex. 2 | —CH$_2$—CH$_3$ | 73% (5) | | |
| Ex. 3 | —(CH$_2$)$_2$—CH$_3$ | 71% (5) | | |
| Ex. 4 | —(CH$_2$)$_3$—CH$_3$ | 60% (5) | | |
| Ex. 5 | —CH$_2$—CH(CH$_3$)$_2$ | 65% (5) | | |
| Ex. 6 | —(CH$_2$)$_2$—OCH$_3$ | 52% (5) | | |
| Ex. 7 | —CH$_2$—CH=CH$_2$ | 66% (5) | | |
| Ex. 8 | —CH=CH$_2$ | 65% (5) | | |
| Ex. 9 | —(CH$_2$)$_2$—OH | 27% (5) | 93% (11) | 29% (11) |
| D * | — | — | 84% (6) | 15% (6) |

Note:
The number in brackets indicates the dose administered in mg/kg.
* D is the compound of formula II mentioned in the description.

What is claimed is:

1. 4-Methyl-2-oxo-2H-1-benzopyran-7-yl 5-thio-β-D-xylopyranoside compound, of formula I:

(I)

in which R is a linear, branched or cyclic C$_1$–C$_5$-alkyl group, a monounsaturated C$_2$–C$_3$-alkene group, a C$_2$–C$_3$-hydroxyalkyl group or a C$_3$–C$_6$-alkoxyalkyl group.

2. Compound according to claim 1, wherein R is methyl, ethyl, propyl, 1-methylethyl, cyclopropyl, butyl, 1-metylpropyl, 2-methylpropyl, 1,1-dimethylethyl or pentyl.

3. Compound according to claim 1, wherein R is vinyl or allyl.

4. Compound according to claim 1, wherein R is methoxyethyl, ethoxyethyl, methoxyethoxyethyl or ethoxyethyl.

5. Compound according to claim 1, which it is 4-methyl-2-oxo-2H-1-benzopyran-7-yl 2,3,4-tri-O-ethoxycarbonyl-5-thio-β-D-xylopyranoside.

6. Compound according to claim 1, which it is 4methyl-2-oxo-2H-1-benzopyran-7-yl 2,3,4-tri-O-methoxycarbonyl-5-thio-β-D-xylopyranoside.

7. Method for the preparation of a compound of formula I according to claim 1 in which the group R is a linear, branched or cyclic $C_1$–$C_5$-alkyl group, a monounsaturated $C_2$–$C_3$-alkene group or a $C_3$–$C_6$-alkoxyalkyl group, which comprises the carbonation reaction of 4-methyl-2-oxo-2H-1-benzopyran-7-yl 5-thio-β-D-xylopyranoside of formula II:

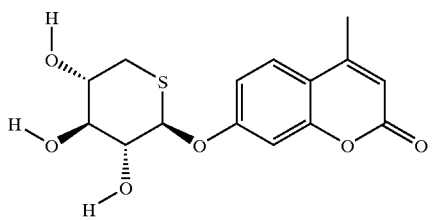

(II)

with a reagent selected from the group consisting of a halogenoformate of formula III:

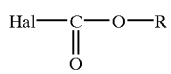

(III)

and a pyrocarbonate of formula IV:

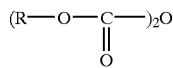

(IV)

in which R is a linear, branched or cyclic $C_1$–$C_5$-alkyl group, a monounsaturated $C_2$–$C_3$-alkene group or a $C_3$–$C_6$-alkoxyalkyl group and Hal is a halogen atom (especially F, Cl or Br).

8. Method for the preparation of a compound of formula I in which R is a $C_2$–$C_3$-hydroxyalkyl group, which comprises the carbonation reaction of 4-methyl-2-oxo-2H-1-benzopyran-7-yl 5-thio-β-D-xylopyranoside of formula II:

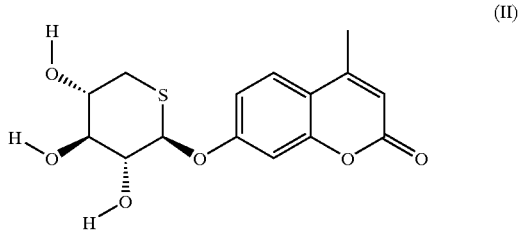

(II)

with a halogenoformate of formula IIIbis:

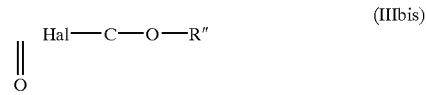

(IIIbis)

in which R" is a $C_2$–$C_3$-hydroxykyl group with its OH function protected and Hal is a halogen atom as defined above, and the resulting compound is then subjected to a deprotection reaction of the OH function of the hydroxyalkyl group by reaction with hydrofluoric acid solution to give the compound of formula I in which R is a $C_2$–$C_3$-hydroxyalkyl group, in an anhydrous solvent, in the presence of an aprotic base, at a temperature of 10° C. to 80° C. for a period of 1 to 10 hours.

9. Pharmaceutical composition, containing a therapeutically effective amount of at least one compound of formula I according to claim 1 in association with a physiologically acceptable excipient.

10. A method of treating disorders of the venous circulation comprising administration of a therapeutically effective amount of a compound of formula I:

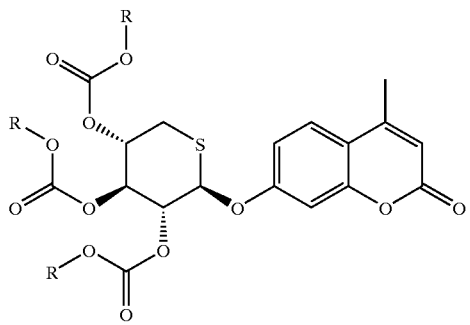

(I)

in which R is a linear, branched or cyclic $C_1$–$C_5$-alkyl group, a monounsaturated $C_2$–$C_3$-alkene group, a $C_2$–$C_3$-hydroxyalkyl group or a $C_3$–$C_6$-alkoxyalkyl group.

* * * * *